United States Patent [19]

Szonntagh

[11] Patent Number: 4,597,778
[45] Date of Patent: Jul. 1, 1986

[54] QUASI-CONTINUOUS SORPTION/DESORPTION ANALYSIS METHOD AND AN APPARATUS UTILIZING THE SAME

[75] Inventor: Eugene L. Szonntagh, Largo, Fla.

[73] Assignee: Honeywell Inc., Minneapolis, Minn.

[21] Appl. No.: 663,108

[22] Filed: Oct. 22, 1984

[51] Int. Cl.[4] .................. B01D 53/04; B01D 35/18
[52] U.S. Cl. ............................... 55/18; 55/59;
      55/162; 55/208; 55/269; 55/387
[58] Field of Search .......... 55/18, 59, 67, 74, 197,
      55/208, 267, 270, 386, 161, 162, 269, 387, 389,
      390; 219/494, 240, 544, 548, 549; 338/34, 35,
      212, 254, 255

[56] References Cited

U.S. PATENT DOCUMENTS

| | | | |
|---|---|---|---|
| 3,200,569 | 8/1965 | Wheeler | 55/269 X |
| 3,496,338 | 2/1970 | Poitras et al. | 219/494 |
| 3,954,616 | 5/1976 | Hunt | 55/267 X |
| 4,237,726 | 12/1980 | Peterson et al. | 55/270 X |
| 4,242,107 | 12/1980 | Jenkins | 55/18 |
| 4,269,611 | 5/1981 | Anderberg | 55/208 X |
| 4,293,316 | 10/1981 | Block | 55/270 X |
| 4,392,870 | 7/1983 | Chieffo et al. | 55/270 X |
| 4,534,777 | 8/1985 | Castleman et al. | 55/270 X |

FOREIGN PATENT DOCUMENTS

| | | | |
|---|---|---|---|
| 873847 | 7/1942 | France | 219/240 |
| 1220064 | 1/1971 | United Kingdom | 55/267 |

Primary Examiner—Robert Spitzer
Attorney, Agent, or Firm—Mitchell J. Halista; Trevor B. Joike

[57] ABSTRACT

A quasi-continuous sorption/desorption analysis method includes the steps of admitting a sample to be analyzed to a stationary sorption/desorption bed for adsorption therein. The flow rate of the sample across the bed is maintained at a high rate for an extended period of time to produce a long sorption time cycle by the sorption bed. Conversely, the subsequent desorption of the sample from the sorption bed is achieved by selectively activating a rapid bed heating element and providing a concurrent low flow rate across the bed to desorb the sample from the sorption bed during a very short desorption time cycle to make the ratio of the sorption/desorption periods as large as possible. The desorbed sample is ultimately conducted to a sample constituent detector for analysis.

A device utilizing the method of the present invention includes a sample inlet flow line having a selectively heatable sorption/desorption bed therein with the flow line being selectively switchable between a high flow rate operation and a low flow rate operation. The flow line is connected to a gas constituent detector system for analysis of a desorbed sample. During the low flow rate operation the sorption bed is selectively operated in a very fast heating cycle. A timing control is used to synchronize the heating operation of the sorption bed during the low flow rate operation of the flow line and the periodic switching of the flow line between the high flow rate and the low flow rate operations.

14 Claims, 6 Drawing Figures

QUASI-CONTINUOUS SORPTION/DESORPTION ANALYSIS METHOD AND AN APPARATUS UTILIZING THE SAME

BACKGROUND OF THE INVENTION

1. Field of the Invention

The present invention relates to gas analysis. Most specifically, the present invention is directed to a method and a device utilizing the method for performing a quasi-continuous sorption/desorption gas analysis.

2. Description of the Prior Art

Convention sorption/desorption devices used in gas analysis used packed columns of sorptive material through which a sample gas is directed to provide an adsorption by the sorptive material of the constituents of interest of the sample gas. Subsequently, the column is heated to desorb the sorbed constituents, and the effluent is directed to a gas detector, e.g., a gas chromatograph, for analysis. Those sorption/desorption devices have exhibited several disadvantages including a slow sorption/desorption cycle, a high electrical power consumption, a bulky structure and a non-continuous operation. Accordingly, the present invention is directed to providing a sorption/desorption apparatus having a fast sorption/desorption cycle which provides a quasi-continuous mode of operation in a structure capable of being miniaturized and which has a low power consumption. Additionally, the present invention provides a sensitivity enhancement of the gas analysis process of at least two orders of magnitude over conventional sorption/desorption analyzers by the use of a unique interrelationship of the sorption/desorption time and the ratio of the sorption/desorption flows. This interrelationship is embodied in the method and apparatus embodying the present invention as described hereinafter.

SUMMARY OF THE INVENTION

The object of the present invention is to provide an improved sorption/desorption analysis method and a device utilizing the same.

In accomplishing this and other objects, there has been provided, in accordance with the present invention, a sorption/desorption gas analysis method including the steps of applying a sample to be analyzed to a sorption/desorption bed during a high rate of flow of the sample across the bed, converting the high flow rate to a relatively low flow rate across the bed and desorbing the sample from the bed by a concurrent rapid heating of the bed. A gas analysis apparatus utilizing this method includes a sample inlet means for connection to a source of a gas to be analyzed, sorption/desorption bed means connected to said inlet means to receive the gas to be analyzed, flow control means for selectively controlling a flow across said sorption/desorption bed means of the gas to be analyzed between a high flow rate and a low flow rate, detector means for analyzing a low flow rate output of said bed means, heater means for selectively heating said sorption/desorption means and control means for selectively energizing said heater means during the low flow rate produced by said flow control means and for periodically switching said flow control means between said high flow rate operation and said low flow rate operation.

BRIEF DESCRIPTION OF THE DRAWINGS

A better understanding of the present invention may be had when the following detailed description is read in connection with the accompanying drawings, in which.

DESCRIPTION OF THE PREFERRED EMBODIMENT

Detailed Description

Figure 1:
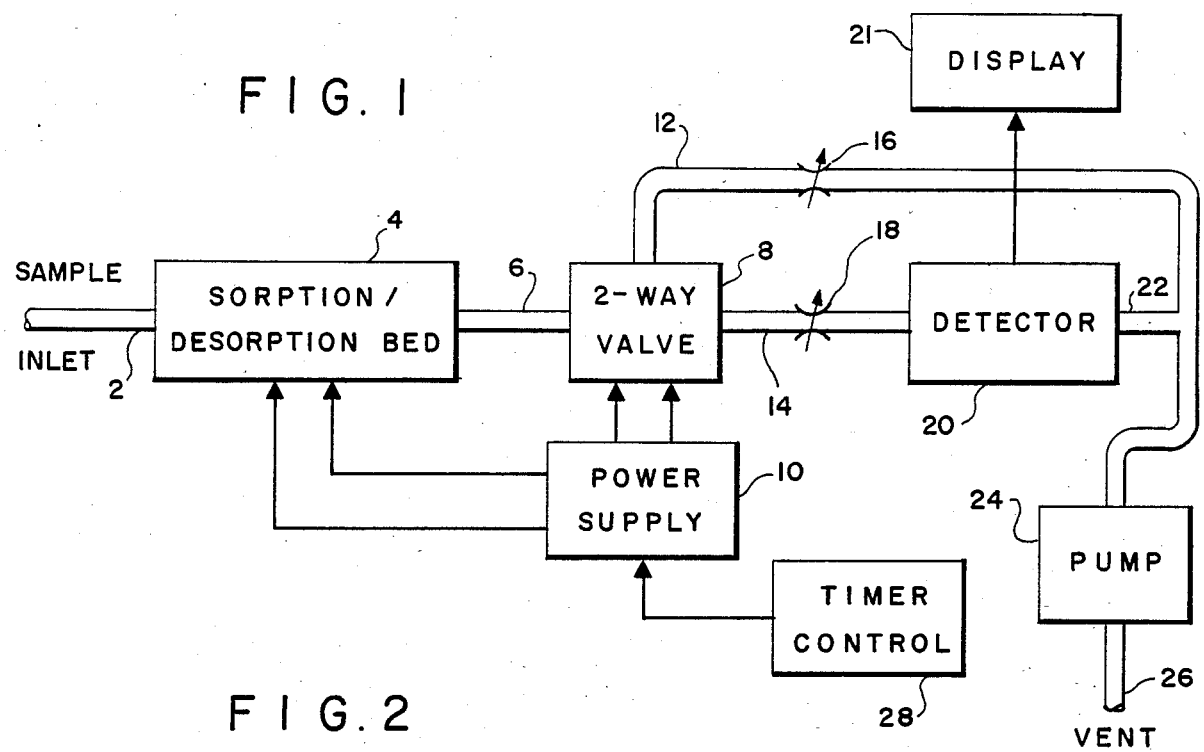
FIG. 1 is a schematic illustration of an example of a first embodiment of an apparatus utilizing the method of the present invention.

Referring to FIG. 1 in more detail, there is shown a schematic illustration of an example of a first embodiment of a gas analyzer apparatus utilizing the method of the present invention and having a sample inlet for admitting a sample to be analyzed to a flow line 2 connected to the inlet of a selectively heatable sorption/desorption bed 4. An outlet from the bed 4 is connected to the inlet 6 of a valve 8 which is selectively actuable by an energizing output signal from a power supply 10. A second output signal from the power supply 10 is to effect the heating of bed 4. The valve 8 is arranged to have a first outlet 12 which is connected to a high flow line, e.g., 900 ml/min. A second outlet 14 from the valve 8 is connected to a low flow line, e.g., 1 ml/min. The flow lines 12, 14 are provided with respective ones of the adjustable restrictions 16, 18 to enable the corresponding flows to be established. The low flow line 14 is connected to an inlet of a gas constituent detector 20 which is used to analyze a gas, e.g., a gas chromatograph. An output signal from the detector 20 is displayed on a suitable display 21. An outlet 22 from the detector 20 is connected to the flow line 12 which is ultimately connected to the inlet of a suction pump 24 for providing a positive displacement of a sample through the flow lines 12,14. An outlet 26 from the pump 24 is connected to a sample vent. A control timer 28 is used to periodically effect the heating of the sorption/desorption bed 4 and the operation of the valve 8 by controlling the output signals from the supply 10.

In operation, the sample to be analyzed is admitted through the inlet line 2 to the sorption bed 4 which is adsorbed for a predetermined period of time. During this adsorption process, the flow rate of the sample is maintained at a high flow rate across the bed 4 and through the flow line 12 to maximize the collection of the sample in the sorption bed 4 and is blocked from entering the detector 20 by the valve 8. At the end of the sorption cycle, the valve 8 is switched by the timer 28 to produce a low flow from the sorption bed 4 through the flow line 14 and the detector 20. Concurrently, the heater in the sorption bed 4 is energized by the timer 28 to produce a very rapid heating of the bed 4 and a desorption of the adsorbed sample from the bed 4. The desorbed sample is analyzed by the detector 20 to produce a detector output signal representative of a detected constituent of the sample. This output signal is applied to a display 21 to produce an indication of the sample analysis. The low flow rate is maintained by the timer 28 for a very short period of time and, subsequently, the valve 8 is actuated by the timer 28 to restore the high flow rate and to block the flow from the detector 20. Concurrently, the heating of the sorption bed 4 is terminated to allow a repetition of the absorbing process of the sample by the bed 4 which is arranged to have a very rapid heating and cooling capability.

Figure 2:
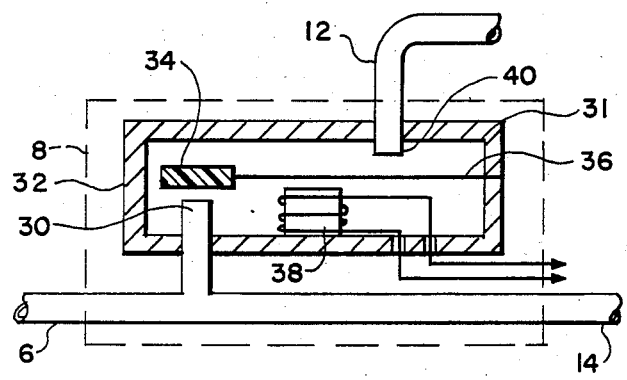
FIG. 2 is a cross-sectional illustration of an example of a valve suitable for use in the apparatus shown in FIG. 1.

In FIG. 2, there is shown a cross-sectional illustration of an example of a valve suitable for use as the valve shown in FIG. 1. The inlet line 6 is connected to a first fluid port 30 located within a chamber 31 defined by a valve housing 32. A port sealing flapper 34 in the form of a resilient pad is operatively with the port 30 and is mounted on a free end of a flexible ferromagnetic arm 36 having its other end attached to the housing 32. An electromagnetic field producing coil 38 is located adjacent to the arm 36 to attract the arm 36 thereto upon an energization of the coil 38. Electrical connections to the coil 38 are provided through fluid-tight electrical feed-throughs in the wall of the housing 32. A second fluid port 40 within the chamber 31 is spaced from the first port 30 and is connected to the second flow line 12. Thus, an energization of the coil 38 by a selective operation of the power supply 10 is effective to displace the flapper 34 against the first port 30 to restrict the flow in the flow line 6 to the low flow defined by the flow line 14 and the restriction 18. Conversely, a deenergization of the coil 38 is effective to allow the arm 36 to position the flapper 34 free of the port 30 as illustrated in FIG. 2. In this position of the flapper 34, the flow line 6 is exposed to the high flow defined by the flow line 12 and the restriction 16. In this arrangement, the flow through the line 14 is essentially bypassed since the flow from the line 6 is channeled by the chamber 31 into the flow line 12.

Figure 3:
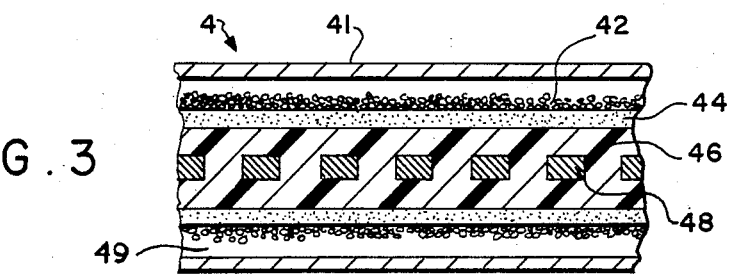
FIG. 3 is a cross-sectional illustration of an example of a suitable sorption/desorption bed for use in the apparatus shown in FIG. 1.

In FIG. 3, there is shown a cross-sectional illustration of an example of a selectively heatable sorption/desorption bed 4 located in flow line housing 41 and having a sorbent powder or particulates 42, e.g., Carbopack, a graphitized carbon black manufactured by Supelco Inc. of Bellefonte, PA, which is held by a suitable adhesive layer 44, e.g., polyimide, to a high temperature, chemically inert polymer laminate 46 having a labrinyth heater film 48 encapsulated therein. The heater 48 is used to provide very fast desorption times of the bed 4 by having a short heat transfer path between the heat source 48 and the sorptive layer 42, by providing a high rate of heat transfer between the heat source 48 and the sorptive layer 42, by having a low heat capacity of the heater 48 and the sorptive layer 42 and by providing a low flow volume 49 within the sorption/desorption device 4. The improved gas analysis method of the present invention is based on a novel interrelationship of the two factors influencing the sensitivity of the sorption/desorption process which are the ratio of sorption/desorption time and the ratio of sorption/desorption flow. The factor of sensitivity enhancement ($F_e$) is:

$$F_e = t_s/t_d \times f_s/f_d,$$

where
- $T_s$ = time duration of sorption
- $T_d$ = time duration of desorption
- $F_s$ = flow rate during sorption and
- $F_d$ = flow rate during desorption In the method of the present invention these parameters are selected and are embodied in an apparatus wherein factors reaching in several orders of magnitude of improvement or enhancement are achieved. Such orders or magnitude increase in sensitivity require extremely fast desorption means to make the sorption/desorption ratio as large as possible when coupled with long sorption times. Since the sorption times are limited by a capacity of the sorption bed and the subsequent need to have a fast desorption cycle, the importance of very short desorption time is of primary concern. The heated sorption bed shown in FIG. 3 includes a very short path between the heating element 48 and the sorption layer 42 and a relatively high heat conductivity material 46 containing the heater and the sorption layer. Further, small dimensions of the sorption bed are used, e.g., the thickness of the heater film 48 is approximately 1 mil and the thickness of the sorption layer 42 is approximately 0.5 mil.

Figure 4:
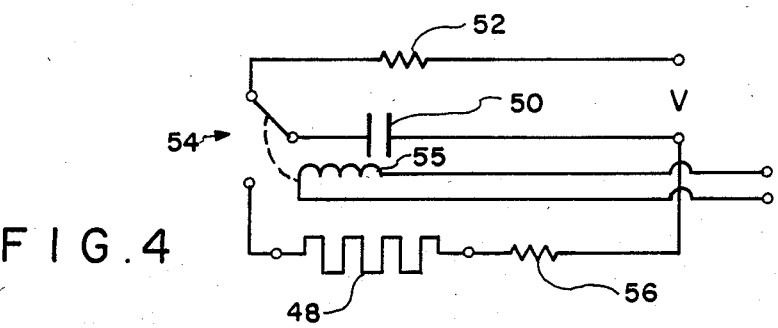
FIG. 4 is a schematic of an energizing circuit for the heating element shown in FIG. 3.

The heater energizing circuit shown in FIG. 4 assists in minimizing the desorption time by utilizing the discharge of a capacitor 50 to provide the energy for a flash-heating of the heating element 48 in the sorption/desorption bed 4. The capacitor 50 is initially charged from the power supply 10 through a charging resistor 52 when a selectively actuable single pole, double throw switch 54 operated by a relay coil 55 is actuated to the position illustrated to provide an electrical connection between one side of the capacitor 50 and one end of the charging resistor 52. The other side of the capacitor 50 and other end of the resistor 52 are continuously connected to the source of power in the power supply 10. When the switch 54 is operated to its other or second position, one side of the capacitor 50 is connected through the heating element 48 and a current limiting resistor 56 to the other side of the capacitor 50 to discharge the capacitor 50 to effect a heating of the element 48. The operation of the capacitor charging and discharging is synchronized with the aforesaid switching of the flow rate by the timer control 28. The resistor 56 may be eliminated if a maximum discharge rate of the capacitor 50 is desired. The capacitor discharge when used in combination with the rapidly heatable sorption bed 4 shown in FIG. 3 is easily capable of producing a heating time of less than one second, and even as low as 0.1 seconds.

While such a discharge of the capacitor 50 will produce a single predetermined temperature of the heating element 48, a plurality of heating temperatures can be produced by utilizing a plurality of capacitors having differing capacity ratings. Each of the capacitors would be charged to the same voltage but would store different amounts of energy. A plurality of switches, such as the switch 54, would be selectively actuated by the timer 28 to charge each of the capacitors and to discharge a selected one through the element 48, i.e., only the capacitor connected to a switch which was actuated to its second position would be connected in series with the element 48. Such a plurality of heating temperatures could be employed in succession in order to separately desorb a succession of sample constituents for analysis with the temperature being correlated to the detected constituent.

As far as flow rates are concerned, the enhancement gain achieved by providing a difference in flow rates is very substantial. For example, if 100 ml/min. flow is used for the sorption cycle and 1 ml/min. for desorption, a ratio of 100 is achievable and if that is combined with a high ratio of sorption to desorption, e.g., 12 sec sorption vs. 0.1 sec. desorption, to give a ratio of 120 which ultimately results in a sensitivity enhancement factor of 12,000. Other higher sensitivity enhancements are, of course, possible by maximizing the aforesaid ratios. The change in flow rate can be achieved by either changing the operation of the pump 24 which is providing a positive displacement of the sample to be tested or by using the valve 8 to switch appropriate flow capillaries in and out, as shown in FIGS. 1 and 2.

In summary, the sample is adsorbed by the sorption bed 4 during a relatively long period of time using a high flow rate across the sorption bed 4 as determined by the valve 8, the restriction 16 and the pump 24. When the sorption cycle is completed, the timer control 28 is arranged to control the output signals from the power supply 10 to energize the coil 38 in the valve 8 to seal the port 30 to impose a low flow rate across the bed 4 and to actuate the switch 54 to discharge the capacitor 50 through the heating element 48. The sample elluted from the bed 4 is directed to the detector 20 to produce an ouput signal representative of a detected sample constituent for display on the display 21. Subsequently, the flow across the bed 4 is reinstated to the high flow rate by the deenergization of the valve 8 by the timer 10. Concurrently, the capacitor 50 is switched to its charging connection by the actuation of the switch 54 by the timer 10. Since the total sorption/desorption cycle time utilizing the method and apparatus of the present invention can be a few seconds, e.g., 10 seconds, a quasi-continuous analysis is thereby achieved, and the sensitivity of the sample analysis is enhanced by the product of the ratio of sorption/desorption time and the ratio of sorption/desorption flow.

Figure 5:
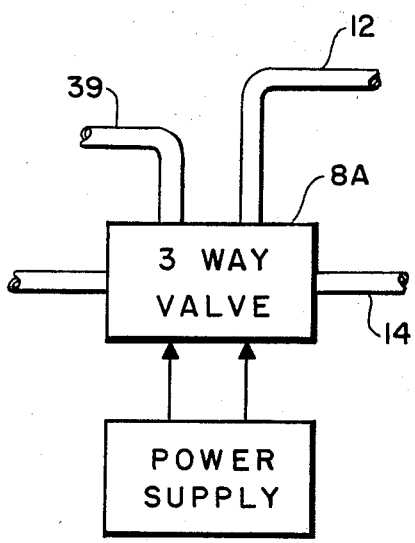
FIG. 5 is a partial schematic illustration of a second embodiment of an apparatus utilizing the method of the present invention and FIG. 6 is a cross-sectional illustration of an example of a valve suitable for use in the apparatus shown in FIG. 5.
Figure 6:
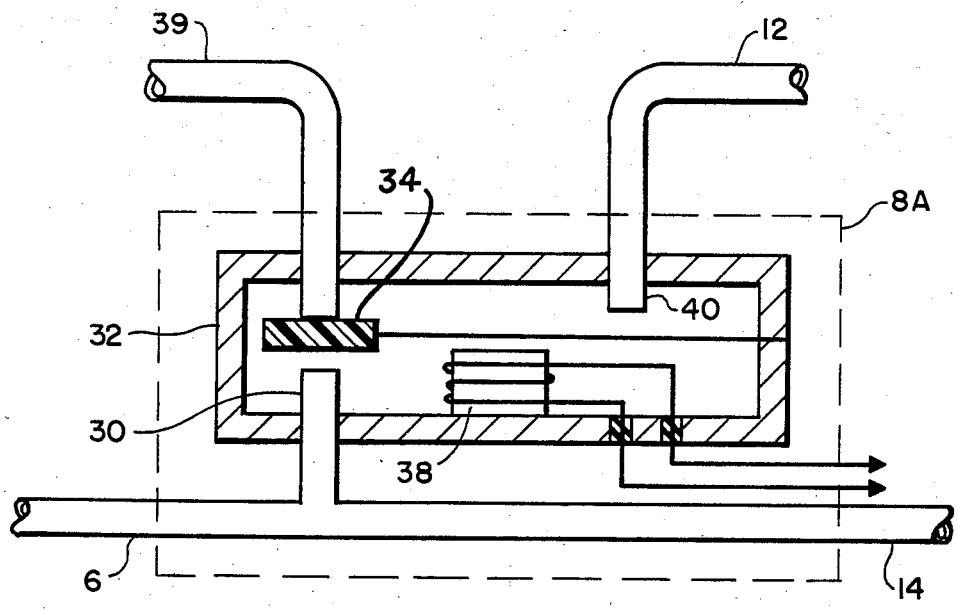

In an alternate embodiment of the apparatus embodying the method of the present invention as illustrated in FIGS. 5 and 6, a low flow rate is continuously maintained through line 14 and the detector 20, to condition the detector 20, e.g., a thermal conductivity bridge, by the constant flow to produce a constant background signal from the detector 20. During the desorption cycle, the sorption/desorption bed 4 is heated by power supply 10 and the coil 38 is energized to produce a movement of the flapper 34 to close the outlet 30 to interrupt the high flow rate across the bed 4 while the low flow rate across the bed 4 is maintained through the line 14. Concurrently, a constant high flow rate is maintained through the valve 8A by means of an auxiliary inlet 39 which is opened by the aforesaid movement of the flapper 34, i.e., the high flow rate is directed through inlet 39 and outlet 12. By concurrently maintaining the low and high rates of flow, a more constant flow rate can be achieved in both the high and low flow lines 12, 14. Such an operation may be particularly useful when using flow sensitive detectors for the detector 20 such as a thermal conductivity type. However, in the alternate embodiment, the flow rate across the bed 4 is still changed from a high flow rate during sorption to a low flow rate during desorption.

Accordingly, it may be seen that there has been provided, in accordance with the present invention, an improved gas analysis method and a device utilizing the same.

The embodiments of the present invention, in which an exclusive property or privilege is claimed are defined as follows:

1. A method for gas analysis including the steps of applying a sample of a gas to be analyzed across a stationary sorption/desorption bed to produce a sorption of the gas by the bed during a high rate of flow of the sample of the gas across the bed by directing the sample of the gas through a sealed gas flow system containing the bed and a high flow rate pipeline converting after a predetermined time period the high flow rate of the sample of the gas to a relatively low flow rate of the sample of the gas across the bed by switching the flow of the sample of the gas to a low flow rate pipeline forming a part of the sealed gas flow system and desorbing the sorbed gas from the bed by a rapid heating of the bed during the low flow rate of the sample of the gas across the bed to produce a flow of all of the desorbed gas through the low flow rate pipeline.

2. A method as set forth in claim 1 and including the further step of applying the desorbed sample to a detector.

3. A method as set forth in claim 1 and including the further step of restoring the high flow rate following the low flow rate operation.

4. A method as set forth in claim 1 and including the further step of periodically alternating between the high flow rate and the low flow rate.

5. A method as set forth in claim 1 wherein the high flow rate is one hundred times the low flow rate.

6. A gas analysis apparatus comprising
   sample inlet means for connection to a source of a gas to be analyzed,
   stationary sorption/desorption bed means including a sorption/desorption bed, a housing for said bed, an input for said housing connected to said inlet means to receive the gas to be analyzed and a housing output,
   flow control means connected to said housing output and including a low flow rate pipeline and a high flow rate pipeline and a flow switching means for selectively controlling a flow across said sorption/desorption bed of the gas to be analyzed between a high flow rate and a low flow rate by switching the flow of the gas to be analyzed between said high flow rate pipeline and said low flow rate pipeline, said housing, said housing input and output, said low flow rate pipeline, said high flow rate pipeline and said flow switching means forming a sealed gas flow system,
   detector means connected to said low flow rate pipeline for analyzing a low flow rate output of the gas to be analyzed from said bed means and all of the gas desorbed from said bed,
   heater means for selectively heating said sorption/desorption bed and
   control means for selectively energizing said heater means during a low flow rate state of said flow control means to desorb a sorbed gas from said bed and for switching said flow control means to direct said flow of the gas to be analyzed between said high flow rate and said low flow rate.

7. A gas analysis apparatus as set forth in claim 6 wherein said control means includes timer means for periodically switching said flow control means between said high flow rate and said low flow rate.

8. An apparatus as set forth in claim 6 wherein said flow switching means includes valve means for switching a flow of the gas to be analyzed between said low flow rate pipeline and said high flow rate pipeline.

9. An apparatus as set forth in claim 6 wherein said heater means includes a resistive heating element, a capacitor means and switch means for selectively switching said capacitor in series with said element to produce a discharge of said capacitor through said element to achieve a desired temperature of said sorption/desorption means.

10. An apparatus as set forth in claim 9 wherein said capacitor means comprises a single capacitor.

11. An apparatus as set forth in claim 9 wherein said capacitor means comprises a plurality of differing capacity capacitors and said switch means is effective to successively connect each of said capacitors in series with said element to achieve a series of correlated temperatures of said sorption/desorption means.

12. An apparatus as set forth in claim 6 wherein said flow control means includes a pump means connected to said high flow rate pipeline and said low flow rate pipeline to induce respective flows of the gas to be analyzed therein.

13. An apparatus as set forth in claim 12 wherein said pump means includes a suction pump.

14. An apparatus as set forth in claim 12 wherein said high flow rate pipeline includes a high flow rate restriction and said low flow rate pipeline includes a low flow rate restriction to control the respective flows therein.

* * * * *